(12) United States Patent
Gately et al.

(10) Patent No.: US 6,590,114 B2
(45) Date of Patent: Jul. 8, 2003

(54) CONVERSION OF CYCLOPENTADIENYL SILYL AMINES TO ORGANOMETALLIC COMPLEXES COMPRISING TITANIUM BISALKOXY MOIETY OR TITANIUM DICHLORIDE MOIETY

(75) Inventors: Daniel A. Gately, Berthoud, CO (US); Jeffrey M. Sullivan, Loveland, CO (US); Karin A. Voll Barclay, Boulder, CO (US); Dawn A. Arkin, Longmont, CO (US)

(73) Assignee: Boulder Scientific Company, Mead, CO (US)

( * ) Notice: Subject to any disclaimer, the term of this patent is extended or adjusted under 35 U.S.C. 154(b) by 75 days.

(21) Appl. No.: 10/045,209

(22) Filed: Nov. 9, 2001

(65) Prior Publication Data

US 2003/0092926 A1 May 15, 2003

(51) Int. Cl.[7] .............................. C07F 17/00; C07F 7/00
(52) U.S. Cl. ................................ 556/11; 556/7; 556/12; 556/22; 556/28; 556/53; 502/103; 526/160; 526/943
(58) Field of Search .................................. 556/7, 11, 12, 556/22, 28, 53; 502/103; 526/160, 943

(56) References Cited

U.S. PATENT DOCUMENTS

| | | | | | |
|---|---|---|---|---|---|
| 5,491,246 | A | * | 2/1996 | Rosen et al. | 556/7 |
| 5,504,223 | A | * | 4/1996 | Rosen et al. | 556/7 |
| 5,703,257 | A | * | 12/1997 | Rosen et al. | 556/7 |

* cited by examiner

Primary Examiner—Porfirio Nazario-Gonzalez
(74) Attorney, Agent, or Firm—Edward S. Irons

(57) ABSTRACT

Conversion of cyclopentadienyl or indenyl compounds to titanium organometallic complexes by treatment with titanium tetraalkoxides is described.

14 Claims, No Drawings

CONVERSION OF CYCLOPENTADIENYL SILYL AMINES TO ORGANOMETALLIC COMPLEXES COMPRISING TITANIUM BISALKOXY MOIETY OR TITANIUM DICHLORIDE MOIETY

FIELD OF THE INVENTION

This invention relates to titanium organometallic complexes which comprise a titanium bisalkoxy moiety or a titanium dichloride moiety.

BACKGROUND OF THE INVENTION

U.S. Pat. Nos. 5,491,246 and 5,504,223 describe the treatment of $Me_4C_5SiMe_2N^t\text{-}bu[MgCl]_2(DME)_n$ with titanium tetraisopropoxide to provide $Me_4C_5SiMe_2N^tBuTi(OiPr)_2$ which may be treated with $SiCl_4$ to yield the corresponding dichloride.

DEFINITIONS

In this specification, the following expressions have the meanings set forth hereinafter:

(1) Cyclopentadienyl means any substituted or unsubstituted cyclopentadienyl compound, group or moiety, including but not limited to any alkylcyclopentadienyl, any indenyl, or any alkyl indenyl compound, group or moiety having one or more $C_1$ to $C_{10}$ alkyl ring substituents.

(2) Alkoxide means any radical or group having the formula —OR, wherein R is an alkyl group.

(3) Cyclopentadienyl silyl amine means a compound of Formula

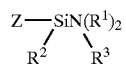

in which Z is a cyclopentadienyl group or moiety and each of $R^1$, $R^2$ and $R^3$ is independently, the same or a different alkyl group, preferably a $C_1$ to $C_{10}$ alkyl group.

SUMMARY OF THE INVENTION

Pursuant to this invention, an alkali metallide of a cyclopentadienyl silyl amine is reacted with a titanium tetraalkoxide $Ti(OR)_4$ in which R is a $C_1$ to $C_{10}$ alkyl group, preferably an isopropyl group. The reaction mixture contains the desired bisalkoxide and, as a by-product, an alkali metal alkoxide which may be isolated or converted in situ to an insoluble alkali metal halide to facilitate removal by filtration. The filtrate contains the desired bisalkoxide which may be converted to the corresponding dichloride by treatment with a halogenating agent, e.g., $SiCl_4$.

DESCRIPTION OF THE INVENTION

The treatment of a silyl amine with $Ti(OR)_4$ may be accomplished in any solvent or medium in which the desired titanium bisalkoxide is soluble. Preferred solvents or media are about 10% to 25% by weight mixtures of ethyl ether and a $C_6$ to $C_8$ hydrocarbon. The treatment may be accomplished at a temperature of from about −20° to −10° C. The conversion of the alkali metal alkoxide by-product to an alkali metal halide insoluble in the solvent contained in the titanium bisalkoxide synthesis reaction mixture is appropriately conducted at a temperature of from about −35° to −20° C. Conversion of the bisalkoxide to the corresponding dichloride may be accomplished in situ in the synthesis reaction mixture at a temperature of −20° C. to room temperature or refluxing temperature. Useful halogenating agents include $SiCl_4$, $BCl_3$, and $AlCl_3$.

EXAMPLE 1

2-Me-indenyl $SiMe_2NH^tBu$ is dilithiated by treatment with butyllithium, e.g., in a 50 weight percent hexane/ether medium at −20° C. See Equation 1:

Equation 1

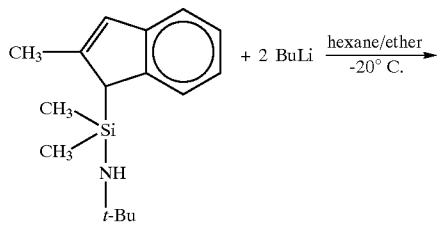

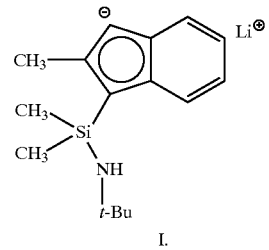

I.

The dilithiated silyl amine is treated with titanium tetraisopropoxide at a temperature of −35° C., wherein a reaction mixture comprising indenyl $SiMe_2NH^tBu$ titanium isopropoxide and lithium isopropoxide is produced. See Equation 2:

Equation 2

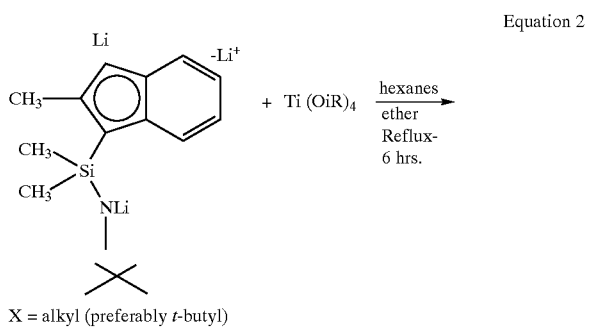

X = alkyl (preferably t-butyl)

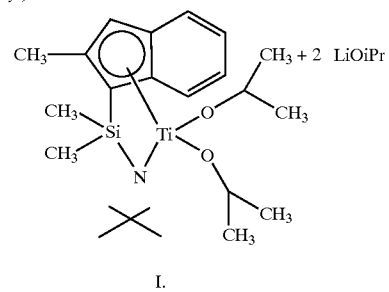

I.

The reaction mixture is treated with $SiCl_4$ in an amount, e.g., 0.6 equiv, sufficient to convert LiOiPR in situ to LiCl which is removed by filtration. A hexane wash of the cake may be combined with the mother liquor which is a solution of the desired titanium bisisopropoxide complex in hexanes/ether.

1.5 equivalents of SiCl$_4$ are added to the LiCl-free mother liquor which contains the titanium bis(isopropoxide) complex to provide a second reaction mixture which is refluxed for six hours, and cooled to precipitate the desired titanium dichloride complex for removal by filtration. The cake is washed with hexanes. Titanium dichloride complex yield= 70% to 80% (based on the silyl amine).

We claim:

1. A method which comprises:
   (i) providing a first reaction mixture comprising a solution of a titanium bisalkoxide complex and an alkali metal alkoxide,
      wherein said step (i) first reaction mixture is provided by treating a cyclopentadienyl silyl amine alkali metallide with a titanium tetraalkoxide in a non-interfering medium in which said titanium bisalkoxide complex and said alkali metal alkoxide are soluble,
   (ii) treating said alkali metal alkoxide in said first reaction mixture with a halogenating agent to produce a second reaction mixture
      wherein said alkali metal alkoxide is converted to an alkali metal halide insoluble in said step (i) non-interfering medium contained in said first reaction mixture, and
   (iii) removing said insoluble alkali metal halide from said second reaction mixture
      wherein a mother liquor containing a solution of said titanium bisalkoxide complex in said step (i) non-interfering medium is produced.

2. The method of claim 1 further comprising a step
   (iv) treating said step (iii) solution of said titanium bisalkoxide complex with a halogenating agent
      wherein a third reaction mixture comprising an organometallic complex including a titanium dihalide moiety is produced.

3. The method of claim 1 wherein said step (i) cyclopentadienyl silyl amine alkali metallide is lithiated 2-methyl indenyl SiMe$_2$NH$^t$bu.

4. In a method wherein a cyclopentadienyl compound is treated in a non-interfering medium with a titanium tetraalkoxide and wherein said treatment provides a reaction mixture comprising a cyclopentadienyl bisalkoxide and an alkali metal alkoxide in solution in said non-interfering medium, the improvement which comprises converting said alkali metal alkoxide in said non-interfering medium to an alkali metal halide.

5. The claim 1 method wherein said titanium tetraalkoxide has the formula Ti(OR)$_4$ in which R is an alkyl group.

6. The claim 1 method wherein step (i) treating is accomplished at a temperature of −35° to −20° C.

7. The claim 4 method in which said cyclopentadienyl compound is an alkyl cyclopentadienyl compound having at least one C$_1$ to C$_{10}$ alkyl ring substituent.

8. A method which comprises:
   (i) providing a first reaction mixture comprising a solution of a titanium bisalkoxide complex and an alkali metal alkoxide,
      wherein said step (i) first reaction mixture is provided by treating a cyclopentadienyl silyl amine alkali metallide with a titanium tetraalkoxide in a non-interfering medium in which said titanium bisalkoxide complex and said alkali metal alkoxide are soluble, and
   (ii) separating said alkali metal alkoxide from said first reaction mixture
      wherein a mother liquor containing a solution of said titanium bisalkoxide complex in said step (i) non-interfering medium is produced.

9. A method which comprises:
   (i) providing a first reaction mixture comprising a solution of a titanium bisalkoxide complex and an alkali metal alkoxide,
      wherein said step (i) first reaction mixture is provided by treating a cyclopentadienyl silyl amine alkali metallide with a titanium tetraalkoxide in a non-interfering medium in which said titanium bisalkoxide complex and said alkali metal alkoxide are soluble,
   (ii) treating said alkali metal alkoxide in said first reaction mixture with a halogenating agent to produce a second reaction mixture
      wherein said alkali metal alkoxide is converted to an alkali metal halide insoluble in situ in said step (i) non-interfering medium contained in said first reaction mixture, and
   (iii) removing said insoluble alkali metal halide from said second reaction mixture
      wherein a mother liquor containing a solution of said titanium bisalkoxide complex in said step (i) non-interfering medium is produced.

10. The method of claim 1 wherein said step (ii) halogenating agent is SiCl$_4$.

11. The method of claim 1 wherein said non-interfering medium is a mixture of ethyl ether and a C$_6$ to C$_8$ hydrocarbon.

12. The method of claim 1 wherein said mixture contains 10% to 25% by weight of said C$_6$ to C$_8$ hydrocarbon.

13. The method of claim 1 wherein said step (i) cyclopentadiene silyl amine alkali metallide has the formula

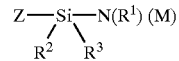

wherein Z is a cyclopentadienyl group or moiety, each of R$^1$, R$^2$ and R$^3$ is the same or a different C$_1$ to C$_{10}$ alkyl group, and M is an alkali metal.

14. The method of claim 1 wherein said alkali metal alkoxide is a lithium alkoxide.

* * * * *